United States Patent
Harada et al.

(10) Patent No.: US 11,384,334 B2
(45) Date of Patent: Jul. 12, 2022

(54) POLYMER GEL FOR MEDIUM, MEDIUM, AND METHOD AND KIT FOR CULTURING CELLS

(71) Applicants: Osaka University, Suita (JP); Kyoto University, Kyoto (JP)

(72) Inventors: Akira Harada, Suita (JP); Yoshinori Takashima, Suita (JP); Masaki Nakahata, Suita (JP); Motomu Tanaka, Kyoto (JP); Marcel Hoerning, Kyoto (JP)

(73) Assignees: Osaka University, Suita (JP); Kyoto University, Kyoto (JP)

( * ) Notice: Subject to any disclaimer, the term of this patent is extended or adjusted under 35 U.S.C. 154(b) by 644 days.

(21) Appl. No.: 16/320,622

(22) PCT Filed: Jul. 25, 2017

(86) PCT No.: PCT/JP2017/026832
§ 371 (c)(1),
(2) Date: Apr. 3, 2019

(87) PCT Pub. No.: WO2018/021289
PCT Pub. Date: Feb. 1, 2018

(65) Prior Publication Data
US 2019/0225936 A1 Jul. 25, 2019

(30) Foreign Application Priority Data

Jul. 28, 2016 (JP) .............................. JP2016-148725

(51) Int. Cl.
*C12N 5/00* (2006.01)
*C12N 1/00* (2006.01)
*C12M 3/00* (2006.01)
*C08F 220/56* (2006.01)

(52) U.S. Cl.
CPC .......... *C12N 5/0068* (2013.01); *C08F 220/56* (2013.01); *C12M 3/00* (2013.01); *C12N 1/00* (2013.01); *C12N 2533/30* (2013.01); *C12N 2537/10* (2013.01)

(58) Field of Classification Search
CPC .................................................. C12N 5/0068
See application file for complete search history.

(56) References Cited

U.S. PATENT DOCUMENTS

| 2006/0003442 A1 | 1/2006 | Gong et al. |
| 2013/0172479 A1 | 7/2013 | Harada et al. |
| 2015/0073091 A1 | 3/2015 | Harada et al. |
| 2015/0259579 A1 | 9/2015 | Harada et al. |
| 2018/0133986 A1 | 5/2018 | Harada et al. |

FOREIGN PATENT DOCUMENTS

| EP | 2292691 A1 | 3/2011 |
| JP | 2013-233101 A | 11/2013 |
| JP | 2016-103982 A | 6/2016 |
| WO | 2012/036069 A1 | 3/2012 |
| WO | 2013/162019 A1 | 10/2013 |
| WO | 2016/163550 A1 | 10/2016 |

OTHER PUBLICATIONS

H. Wang et al., "Adaptable Hydrogel Networks with Reversible Linkages for Tissue Engineering," Advanced Materials, 2015, vol. 27, pp. 3717-3736.
T. Kakuta et al., "Adhesion between Semihard Polymer Materials Containing Cyclodextrin and Adamantane Based on Host—Guest Interactions," Macromolecules, 2015, vol. 48, pp. 732-738.
Y. Lan et al., "A supramolecular route towards core-shell polymeric microspheres in water via cucurbit[8]uril complexation," Chemical Communications, 2012, vol. 48, pp. 8757-8759.
D. Patra et al., "Formation and Size Tuning of Colloidal Microcapsules via Host-Guest Molecular Recognition at the Liquid-Liquid Interface," Langmuir, 2009, vol. 25, No. 24, p. 13852-13854.
D. D. McKinnon et al., "Biophysically Defined and Cytocompatible Covalently Adaptable Networks as Viscoelastic 3D Dell Culture Systems," Advanced Materials, 2014, vol. 26, pp. 865-872.
A. J. Engler et al., "Matrix Elasticity Directs Stem Cell Lineage Specification," Cell, 2006, vol. 126, pp. 677-689.
N. Yamada et al., "Thermo-responsive polymeric surfaces; control of attachment and detachment of cultured cells," Makromol. Chem. Rapid Commun., 1990, vol. 11, pp. 571-576.
International Search Report dated Oct. 10, 2017, issued for PCT/JP2017/026832.
Extended European Search Report dated Jun. 17, 2020, issued for corresponding EP Patent Application No. 17834295 2.

*Primary Examiner* — Bin Shen
(74) *Attorney, Agent, or Firm* — Locke Lord LLP; James E. Armstrong, IV; Nicholas J. DiCeglie, Jr.

(57) ABSTRACT

Provided are: a polymer gel for a medium, and a medium in which the stiffness of the polymer gel can be easily and reversibly changed and the shape of cells can be controlled according to the stiffness of the gel; and a method for culturing cells using the medium. The polymer gel for a medium contains a solvent and a crosslinked structure that is crosslinked by reversible bonds. The stiffness of the polymer gel for a medium can be easily and reversibly changed. Accordingly, when the polymer gel for a medium according to the present invention is used, cell morphology and function can be reversibly controlled according to the stiffness of the gel.

4 Claims, 3 Drawing Sheets

POLYMER GEL FOR MEDIUM, MEDIUM, AND METHOD AND KIT FOR CULTURING CELLS

TECHNICAL FIELD

The present invention relates to a polymer gel for a medium; a medium; a method for culturing cells; and a kit for culturing cells.

BACKGROUND ART

In recent years, with the rapid development of research in the field of regeneration medicine etc., and applications thereof, there is an urgent need to construct a technique for easily culturing desired tissue at low cost. Therefore, research and development for controlling cell culture and cell differentiation are actively conducted from a variety of perspectives.

In the field of regenerative medicine, the kind of medium for culturing stem cells is known to significantly affect the differentiation of multipotential cells. For example, in recent research in which stem cells were cultured on substrates whose stiffness was statically controlled, cellular differentiation was reported to vary according to the stiffness of the substrate used (see, for example, Non-patent Literature (NPL) 1). As disclosed in such reports, polyacrylamide-based gels have been used as substrates whose stiffness can be adjusted by controlling the structure etc. of the polymer gels. As in the technique described above, understanding the influence of cell culture substrate characteristics on cell behaviors has become an extremely interesting field of research in regenerative medicine and tissue engineering, etc.

CITATION LIST

NPL

NPL 1: Cell 126, 677-689, Aug. 25, 2006

SUMMARY OF INVENTION

Technical Problem

However, the stiffness of a substrate crosslinked by covalent bonds, such as a conventional acrylamide gel, as in the above technique can only be controlled statically (for example, by adjusting the degree of crosslinking, molecular weight, concentration, etc.). Therefore, the stiffness of the substrate cannot be changed at the necessary timing. Accordingly, there is no degree of freedom for dynamically controlling cell culture behaviors; furthermore, many problems remain unsolved from the viewpoint of practical use. It is expected from these viewpoints that an unprecedented cell differentiation control technique can be established if the stiffness of a substrate can be adjusted dynamically at the desired timing.

The present invention has been made in view of the above. An object of the present invention is to provide a medium comprising a polymer gel whose stiffness can be easily and reversibly changed, and which enables the control of cell shape according to the stiffness of the polymer gel. Another object of the present invention is to provide a method for culturing cells using the medium, and a kit comprising the medium as a component.

Solution to Problem

The present inventors conducted extensive research to achieve the above object. As a result, the inventors found that the above object can be achieved by containing, as an essential component, a crosslinked structure comprising reversible bonds. The inventors also found that the above object can be achieved by culturing cells while controlling the crosslinking density of the crosslinked structure comprising reversible bonds. The present invention has thus been accomplished.

Specifically, the present invention includes, for example, the following itemized subject matter.

Item 1. A medium, comprising a solvent and a crosslinked structure that is crosslinked by reversible bonds.

Item 2. The polymer gel for a medium according to Item 1, wherein the reversible bonds are at least one member selected from the group consisting of bonds between host groups and guest groups, hydrophobic interactions, hydrogen bonds, ionic bonds, coordinate bonds, Π-electron interactions, and intermolecular interactions other than these.

Item 3. The polymer gel for a medium according to Item 1 or 2, wherein the reversible bonds are bonds between host groups and guest groups.

Item 4. The polymer gel for a medium according to any one of Items 1 to 3, wherein the crosslinked structure is a polymer comprising:

a repeating structural unit represented by formula (1a)

(wherein Ra is hydrogen or methyl; $R^1$ is a divalent group formed by removing one hydrogen atom from a monovalent group selected from the group consisting of hydroxyl, thiol, alkoxy optionally having one or more substituents, thioalkoxy optionally having one or more substituents, alkyl optionally having one or more substituents, amino optionally having one substituent, amide optionally having one or more substituents, aldehyde, and carboxyl; and $R^A$ is a host group);

a repeating structural unit represented by formula (2a):

wherein Ra is as defined above in formula (1a), that is, Ra is hydrogen or methyl; $R^2$ is a divalent group formed by removing one hydrogen atom from a monovalent group selected from the group consisting of hydroxyl, thiol, alkoxy optionally having one or more substituents, thioalkoxy optionally having one or more substituents, alkyl optionally having one or more substituents, amino optionally having one substituent, amide optionally having one or more substituents, aldehyde, and carboxyl; and $R^B$ is a guest group); and a repeating structural unit represented by formula (3a):

(wherein Ra is as defined above in formula (1a); $R^3$ is halogen, hydroxyl, thiol, amino optionally having one substituent, carboxyl optionally having one substituent, or amide optionally having one or more substituents).

Item 5. A medium comprising the polymer gel according to any one of Items 1 to 4.

Item 6. A cell culture method comprising culturing cells in the medium according to Item 5.

Item 7. The cell culture method according to Item 6, further comprising adding to the medium a competitive substance having a property of inhibiting formation of the reversible bonds.

Item 8. The cell culture method according to Item 7, wherein the concentration of the competitive substance added to the medium is increased or decreased.

Item 9. The cell culture method according to Item 7 or 8, wherein the concentration of the competitive substance contained in the medium is adjusted to 10 mol/L or less.

Item 10. A kit comprising the medium according to Item 5.

Advantageous Effects of Invention

The polymer gel for a medium according to the present invention, which comprises a solvent and a structure that is crosslinked by reversible bonds, can easily and reversibly change its stiffness. Therefore, when the polymer gel for a medium according to the present invention is used, cell shape and function can be reversibly controlled according to the stiffness of the polymer gel. Therefore, the polymer gel for a medium is a material suitable as a medium for culturing various cells.

The method for culturing cells according to the present invention, which uses the medium described above, can control cell shape by a simple method, while adjusting the stiffness of the medium.

The kit according to the present invention, which comprises the medium described above, is suitable for culturing various cells.

DESCRIPTION OF EMBODIMENTS

Embodiments of the present invention are described below in detail. In the present specification, the expressions "containing" and "comprising" include the concepts of "containing," "comprising," "essentially consisting of," and "consisting only of."

Polymer Gel for Medium

The polymer gel for a medium according to this embodiment comprises a solvent and a crosslinked structure that is crosslinked by reversible bonds. This polymer gel is formed in such a manner that formation and cleavage of reversible bonds can be controlled, for example, by the addition of a competitive substance as described below. Accordingly, the polymer gel is a material that can dynamically control the stiffness (elasticity) of the polymer gel, i.e., its physical properties, such as elastic modulus. In this way, the stiffness of the polymer gel according to this embodiment can be easily and reversibly changed; therefore, when cells are cultured in a medium formed by using this polymer gel, cell shape and function can be easily controlled according to the stiffness of the polymer gel.

The morphology of the polymer gel is described in detail below. In this specification, the polymer gel according to this embodiment is sometimes simply referred to as the "polymer gel."

The polymer gel comprises, as a matrix, a crosslinked structure that is crosslinked by reversible bonds, and is in the form of a gel due to the presence of a solvent in the matrix. For example, the crosslinked structure is in a state swollen with a solvent.

The crosslinked structure has a structure such that polymer chains are formed into a three-dimensional network structure. The crosslinked structure having such a three-dimensional network structure is formed by crosslinking polymer chains to each other.

In the polymer gel according to this embodiment, the crosslinked structure is formed by reversible bonds as crosslinking points.

The term "reversible bonds" referred to herein means that the bonds are formed and cleaved reversibly. Reversible bonds refer to, for example, non-covalent bonds.

More specific examples of the reversible bonds are preferably at least one member selected from the group consisting of bonds between host groups and guest groups, hydrophobic interactions, hydrogen bonds, ionic bonds, coordinate bonds, Π-electron interactions, and intermolecular interactions other than these. Formation and cleavage of these bonds can all be easily controlled.

The reversible bonds are particularly preferably bonds between host groups and guest groups, i.e., so-called host-guest interactions. This is because when the reversible bonds are formed by such host-guest interactions, controlling the formation and cleavage of such bonds is particularly easy; and stiffness of the polymer gel, particularly elastic modulus, can be easily adjusted to a desired range. For example, when the reversible bonds are formed by host-guest interactions, the formation and cleavage of such bonds can be easily controlled by the addition and removal of a competitive substance, as described below.

Accordingly, the crosslinked structure contained as a matrix in the polymer gel is preferably formed into a three-dimensional network structure having host-guest complexes as crosslinking points.

The host-guest complexes can be formed by, for example, but are not limited to, hydrophobic interactions between host molecules and guest molecules, hydrogen bonds, intermolecular forces, electrostatic interactions, coordinate bonds, Π-electron interactions, and the like.

The kind of polymer chain forming the crosslinked structure is not particularly limited.

The polymer chain, for example, has a structure in which functional group(s) capable of reversibly bonding are present in its side chain(s). Examples of functional group(s) capable of reversibly bonding include functional groups capable of forming host-guest interactions, hydrophobic interactions, hydrogen bonds, ionic bonds, coordinate bonds, Π-electron interactions, and intermolecular interactions other than these.

Since the polymer gel contains polymer chains that have, in side chains thereof, functional groups capable of reversibly bonding, polymer chains thereof are crosslinked to each other to form a network structure. This crosslinked structure can be formed in such a manner that a reversibly bondable functional group in a side chain of one polymer chain is bound to a reversibly bondable functional group in a side chain of another polymer chain, and the resulting bonding site functions as a crosslinking point.

More specific examples of polymer chains are polymer chains having a structure such that host molecules and guest molecules are covalently bound to side chains of the polymer chains. When host molecules and guest molecules are covalently bound to polymer side chains, each of the host molecules and the guest molecules is bound, for example, in the form of a monovalent group obtained by removing, for example, hydrogen or hydroxyl groups from the host molecules and the guest molecules. In other words, polymer chains can have host groups and guest groups in their side chains, and the host groups and guest groups are both covalently bound to polymer side chains.

The kinds of host molecules and guest molecules are not particularly limited, as long as they are molecules capable of forming host-guest complexes, and are non-cytotoxic.

Examples of host molecules include at least one member selected from the group consisting of α-cyclodextrin, β-cyclodextrin, γ-cyclodextrin, calix[6]arene sulfonate, calix[8]arene sulfonate, 12-crown-4, 18-crown-6, [6]paracyclophane, [2,2]paracyclophane, cucurbit[6]uril, and cucurbit[8]uril. These molecules may optionally have one or more substituents. Since a polymer having such a host molecule in its side chain as a host group is prone to form a host-guest interaction with a guest group described below, a network structure having a stable crosslinking points is formed, and the stiffness of the polymer gel can be easily controlled.

Examples of guest groups include $C_{4-18}$ alkyl compounds. Specific examples include butane, pentane, hexane, heptane, octane, nonane, decane, undecane, dodecane, tetradecane, pentadecane, hexadecane, heptadecane, octadecane, adamantane, and the like. These compounds may be linear or branched alkyl compounds. The $C_{4-18}$ hydrocarbons may be alkyl to which ferrocene, which is an organometallic complex, is bound as a substituent. Since a polymer having such a guest molecule in its side chain as a guest group is prone to form a host-guest interaction with a host group described above, a crosslinked network having a stable crosslinking points is formed, and the stiffness of the polymer gel can be easily controlled.

From the viewpoint of ease of occurrence of host-guest interactions and ease of adjustment of stiffness, the host molecule is preferably at least one molecule selected from the group consisting of α-cyclodextrin, β-cyclodextrin, and γ-cyclodextrin, or derivatives of any of these cyclodextrins. The cyclodextrin derivatives herein refers to, for example, compounds obtained by replacing hydrogen or hydroxyl group(s) of cyclodextrin with other substituent(s). Examples of such substituents include, but are not limited to, alkyl having 1 to 4 carbon atoms, alkenyl having 1 to 4 carbon atoms, and groups having a C=O bond, such as acetyl.

For the same reasons, the guest group to be used is preferably at least one member selected from the group consisting of n-butyl, n-dodecyl, t-butyl, and adamantyl.

Preferable combinations of a host group and a guest group are as follows. when the host molecule that forms a host group is α-cyclodextrin, the guest group is preferably at least one member selected from the group consisting of n-butyl, n-hexyl, n-octyl, and n-dodecyl; when the host molecule that forms a host group is β-cyclodextrin, the guest group is preferably at least one member selected from the group consisting of adamantyl, adamantyl substituted with hydroxyl, adamantyl substituted with ethyl, and isobornyl; and when the host molecule that forms a host group is γ-cyclodextrin, the guest group is preferably at least one member selected from the group consisting of, for example, n-octyl, n-dodecyl, and cyclododecyl.

As described above, the polymer chains have host groups and guest groups in side chains thereof. The backbone structure of the polymer chains is not particularly limited.

For example, the backbone structure of the polymer chains contained in the crosslinked structure preferably has all of the repeating structural units represented by the above formula (1a), formula (2a), and formula (3a).

A polymer that has all of the repeating structural units represented by formula (1a), formula (2a), and formula (3a) is hereinafter referred to as "polymer A."

The crosslinked structure can comprise one kind, or two or more kinds of polymers. For example, the crosslinked structure may comprise as the polymer only one kind of polymer A, or two or more different kinds of polymer A. As long as the effect of the present invention is not impaired, the crosslinked structure may optionally comprise one or more other polymers containing neither host groups nor guest groups.

Since polymer A has host groups and guest groups in its side chains, crosslinking points due to host-guest interactions are formed to thereby form a crosslinked structure.

When $R^1$ in formula (1a) is a divalent group formed by removing one hydrogen atom from alkoxy, examples of the alkoxy include $C_{1-10}$ alkoxy. The $C_{1-10}$ alkoxy may be linear or branched alkoxy.

When $R^1$ in formula (1a) is a divalent group formed by removing one hydrogen atom from thioalkoxy, examples of the thioalkoxy include $C_{1-10}$ thioalkoxy. The $C_{1-10}$ thioalkoxy may be linear or branched thioalkoxy.

When $R^1$ in formula (1a) is a divalent group formed by removing one hydrogen atom from alkyl, examples of the alkyl include $C_{1-30}$ alkyl. The $C_{1-30}$ alkyl may be linear or branched alkyl.

When $R^1$ in formula (1a) is a divalent group formed by removing one hydrogen atom from amino optionally having one substituent, the nitrogen atom of amino can bind to a carbon atom in the main chain (C—C bond).

When $R^1$ in formula (1a) is amide optionally having one substituent, the carbon atom of amide can bind to a carbon atom in the main chain (C—C bond).

When $R^1$ in formula (1a) is aldehyde, the carbon atom of aldehyde can bind to a carbon atom in the main chain (C—C bond).

When $R^1$ in formula (1a) is carboxyl, the carbon atom of carboxyl can bind to a carbon atom in the main chain (C—C bond).

Examples of $R^A$ in formula (1a) include the host groups described above.

$R^1$ in formula (1a) is preferably formed by removing one hydrogen atom from a monovalent group selected from the group consisting of amide and carboxyl. Specifically, the repeating structural unit represented by formula (1a) preferably has at least one of: a structure having in its side chain an amide group whose hydrogen atom is replaced with $R^A$; and a structure having in its side chain a carboxyl group whose hydrogen atom is replaced with $R^A$. In this case, synthesis of polymer A is easy, and a polymer gel whose stiffness is easily controlled can be obtained.

$R^2$ in formula (2a) is as defined above for $R^1$ in formula (1a), and $R^2$ bonds to the main chain (C—C bond) in the same manner as $R^1$ in formula (1a).

Examples of $R^B$ in formula (2a) include the guest groups described above.

$R^2$ in formula (2a) is preferably formed by removing one hydrogen atom from a monovalent group selected from the group consisting of amide and carboxyl. Specifically, the repeating structural unit represented by formula (2a) preferably has at least one of: a structure having in its side chain an amide group whose hydrogen atom is replaced with $R^B$; and a structure having in its side chain a carboxyl group whose hydrogen atom is replaced with $R^B$. In this case, synthesis of polymer A is easy, and a polymer gel whose stiffness is easily controlled can be obtained.

When $R^3$ in formula (3a) is carboxyl having one substituent, examples include carboxyl whose hydrogen atom is replaced with alkyl (e.g., methyl or ethyl) or hydroxyalkyl (e.g., hydroxymethyl or hydroxyethyl).

When $R^3$ in formula (3a) is amide having at least one substituent, i.e., secondary amide or tertiary amide, such amide includes, for example, amide formed by replacing one or two hydrogen atoms in a primary amide group independently with alkyl (e.g., methyl and ethyl) or hydroxyalkyl (e.g., hydroxymethyl and hydroxyethyl).

$R^3$ in formula (3a) is preferably amino; amide; amide whose hydrogen is replaced with alkyl, hydroxyl, or alkoxyl; carboxyl; or carboxyl whose hydrogen is replaced with alkyl, hydroxyalkyl (e.g., hydroxyethyl), or alkoxyl). In this case, synthesis of polymer A is easy, and a polymer gel whose stiffness is easily controlled can be obtained.

In polymer A, these different repeating structural units may be regularly arranged, or randomly arranged. Specifically, polymer A may be a block copolymer, an alternate copolymer, or a random copolymer. Alternatively, polymer A may be a graft copolymer.

The proportions of repeating structural units of formula (1a), formula (2a), and formula (3a) that form polymer A are not particularly limited. For example, the proportion of the repeating structural unit represented by formula (1a) can be 0.5 to 10 mol %, and the proportion of the repeating structural unit represented by formula (2a) can be 0.5 to 10 mol %, based on the total amount of all of the repeating structural units of polymer A. In this case, interactions between host groups and guest groups readily occur, and polymer A easily forms a crosslinked structure. Therefore, there is an increased tendency that a stable crosslinked structure is obtained, and a polymer gel whose stiffness is easily controlled is formed.

Preferably, the proportion of the repeating structural unit represented by formula (1a) is 1 to 5 mol %, and the proportion of the repeating structural unit represented by formula (2a) is 1 to 5 mol %, based on the total amount of all the repeating structural units of polymer A. It is particularly preferable that the proportion of the repeating structural unit represented by formula (1a) is 2 to 4 mol %, and the proportion of the repeating structural unit represented by formula (2a) is 2 to 4 mol %.

The solvent contained in the polymer gel may be, for example, water. A wide range of other solvents and known cell culture fluids can also be used.

The polymer gel can further contain other additives, as long as the effect of the present invention is not impaired. Examples of other additives include antioxidants, UV absorbers, light stabilizers, various fillers, electrolytes, and the like. With the purpose of improving the chemical properties etc. of polymer materials, the polymer gel may optionally contain a polymeric compound other than the crosslinked structure.

As long as the effect of the present invention is not impaired, the polymer gel may have, in addition to crosslinking points formed by reversible bonds, other crosslinking points formed by covalent bonds.

The shape of the polymer gel is not particularly limited. The polymer gel can be formed so as to fit to the medium used. For example, the polymer gel can be formed into a sheet etc. by known means.

The method for producing a polymer gel is not particularly limited. For example, the polymer gel can be produced by polymerizing at least one polymerizable monomer. The polymerizable monomer is a compound for forming a repeating unit of the polymer gel.

For example, the polymer gel can be produced by a method of polymerizing polymerizable monomers for forming repeating structural units represented by formulas (1a), (2a), and (3a). In this case, the polymer gel can be produced by polymerizing these polymerizable monomers in an aqueous medium in the presence of a polymerization initiator. The polymerizable monomers for forming repeating structural units represented by formula (1a), formula (2a), and formula (3a) are briefly referred to as "monomer (1)," "monomer (2)," and "monomer (3)," respectively.

The polymerizable monomer can be, for example, a mixture of a polymerizable monomer having the host group in the molecular structure, a polymerizable monomer having the guest group in the molecular structure, and a polymerizable monomer containing neither host groups nor guest groups.

Examples of the polymerizable monomer having host groups in the molecular structure ("monomer (1)") include, but are not limited to, (meth)acrylamide-α-cyclodextrin, (meth)acrylamide-β-cyclodextrin, (meth)acrylamide-γ-cyclodextrin, α-cyclodextrin methacrylate, β-cyclodextrin methacrylate, γ-cyclodextrin methacrylate, α-cyclodextrin acrylate, β-cyclodextrin acrylate, γ-cyclodextrin acrylate, hydroxymethyl (meth)acrylamide-α-cyclodextrin, hydroxymethyl (meth)acrylamide-β-cyclodextrin, hydroxymethyl (meth)acrylamide-γ-cyclodextrin, acrylamide methyl-α-cyclodextrin, acrylamide methyl-β-cyclodextrin, and acrylamide methyl-γ-cyclodextrin. Monomer (1) can be prepared by a known method.

The term "(meth)acryl" as used herein refers to acryl or methacryl.

Examples of polymerizable monomers having guest groups in the molecular structure (hereafter referred to as "monomer (2)") include, but are not limited to, n-butyl (meth)acrylate, t-butyl (meth)acrylate, n-hexyl (meth)acrylate, n-dodecyl (meth)acrylate, 1-acrylamide adamantane, N-(1-adamanthyl) (meth)acrylamide, hydroxyadamantyl (meth)acrylate, ethyladamantyl (meth)acrylate, N-benzyl (meth)acrylamide, N-1-naphthylmethyl (meth)acrylamide, isobornyl acrylate, and the like. Styrene can be used in place of monomer (2). Monomer (2) can be produced by a known method.

Examples of the polymerizable monomer having neither host groups nor guest groups (hereinafter referred to as "monomer (3)") include (meth)acrylic acid, (meth)acrylamide, methyl (meth)acrylate, ethyl (meth)acrylate, N,N-dimethylacrylamide, N-isopropyl (meth)acrylamide, N-hydroxymethyl (meth)acrylamide, N-hydroxymethyl (meth)acrylate, 2-hydroxyethyl (meth)acrylamide, 2-hydroxyethyl (meth)acrylate, and the like.

The proportions of polymerizable monomers (1), (2), and (3) can be suitably selected according to characteristics of the desired polymer gel. For example, based on the total amount of polymerizable monomers (1), (2), and (3), the proportion of polymerizable monomer (1) can be 0.5 to 10 mol %, and the proportion of polymerizable monomer (2) can be 0.5 to 10 mol %. In this case, interactions between host groups and guest groups in the obtained polymer readily occur, and a crosslinked structure is easily formed. More preferably, the proportion of polymerizable monomer (1) is 1 to 5 mol %, and the proportion of polymerizable monomer (2) is 1 to 5 mol %, based on the total amount of polymerizable monomers (1), (2), and (3). It is particularly preferable that the proportion of polymerizable monomer (1) is 2 to 4 mol %, and the proportion of polymerizable monomer (2) is 2 to 4 mol %, based on the total amount of polymerizable monomers (1), (2), and (3).

The polymerization reaction of the polymerizable monomers can be performed in an aqueous medium, in particular, in water. In this case, the polymer gel produced comprises a crosslinked structure and water. As long as the formation of the polymer gel is not impaired, the aqueous medium can be a mixed solvent of water and other solvent(s). Examples of such other solvents include hydrophilic solvents having a boiling point higher than water (e.g., DMF, DMSO, etc.). Other examples include organic solvents compatible with water, such as lower alcohol.

Examples of the polymerization initiator used in the reaction of polymerizing the polymerizable monomers include ammonium persulfate (which may be hereinafter referred to as APS), azobisisobutyronitrile (which may be hereinafter referred to as AIBN), 2,2'-azobis[2-(2-imidazolin-2-yl)propane]dihydrochloride (which may be hereinafter referred to as VA-044), 1,1'-azobis(cyclohexanecarbonitrile), di-tert-butyl peroxide, tert-butyl hydroperoxide, benzoyl peroxide, photopolymerization initiators (e.g., Irgacure (registered trademark) series), and the like. The polymerization initiator is preferably APS or VA-044.

The concentration of the polymerization initiator can be 0.5 to 5 mol %, based on the total amount of the polymerizable monomers.

The mixture of the aqueous medium, polymerization initiator, and polymerizable monomer can be prepared by mixing these components in predetermined amounts. When the mixture is to be prepared, monomers (1) and (2) can be mixed with heating beforehand, and the other starting materials can then be mixed thereinto. In this case, the polymerization can proceed with an inclusion complex being formed by host-guest interactions between monomers (1) and (2). Therefore, a polymer gel containing a stable crosslinked structure can be produced.

If necessary, other additives may be added for the polymerization reaction. Examples of such other additives include polymerization accelerators, crosslinking agents, and the like. Examples of polymerization accelerators include N,N,N',N'-tetramethylethylenediamine and the like.

The polymerization reaction can be performed under appropriate conditions according to, for example, the degree of polymerization of monomers used and 10 h half-life temperature of the polymerization initiator. The polymerization reaction can be performed, for example, at 0 to 100° C., and preferably 20 to 25° C. The polymerization reaction time is, for example, 1 to 24 hours, and preferably 12 to 24 hours. When a photopolymerization initiator is used as a polymerization initiator, the polymerization reaction is performed, for example, by irradiating the mixture with UV light at a wavelength of 200 to 400 nm.

The polymerization reaction as described above can form a copolymer resulting from the polymerization of monomers (1), (2), and (3). The copolymer referred to herein corresponds to polymer A described above.

After the polymerization reaction, removal of a potentially toxic monomer or a low molecular polymer, purification, drying, and the like may be performed, if necessary, to thereby produce a polymer gel comprising a crosslinked structure and a solvent.

Another method for producing a polymer gel having host groups and guest groups comprises producing beforehand a polymer containing neither host groups nor guest groups, then allowing this polymer to react with host molecules and guest molecules to introduce host groups and guest groups to side chains of the polymer.

The production method described above is an example of producing a polymer gel comprising a solvent and a crosslinked structure that is crosslinked by host-guest interactions. Polymer gels comprising a solvent and a crosslinked structure that is crosslinked by reversible bonds other than host-guest interactions can also be produced in a similar manner by appropriately changing the polymerizable monomers to be used.

One of the features of the polymer gel thus formed is that its stiffness is easily adjustable. For example, elastic modulus of the polymer gel tends to depend on the number of reversible bonds, which are crosslinking points of the crosslinked structure. Although it depends on the kind of polymer gel, for example, the greater the number of crosslinking points in the crosslinked structure, the harder the polymer gel. That is, as the number of reversible bonds increases, the polymer gel tends to be hard. Accordingly, the stiffness of the polymer gel can be easily adjusted by controlling the formation and cleavage of reversible bonds in the crosslinked structure contained in the polymer gel.

The method for adjusting the stiffness of the polymer gel is not particularly limited, and an appropriate method can be used according to the properties of reversible bonds. When the reversible bonds are bonds between host groups and guest groups, a method comprising adding a competitive substance to the polymer gel in an amount appropriately changed to adjust the stiffness can be used.

The stiffness of the polymer gel having host groups and guest groups is preferably adjusted by a method comprising changing the amount of competitive substance added to the polymer gel. Since this method can promote formation and cleavage of reversible bonds, which are crosslinking points of the crosslinked structure, stiffness of the polymer gel can be precisely controlled.

The "competitive substance" referred to herein means, for example, a substance that has the property of contributing to the formation and cleavage of reversible bonds formed in the crosslinked structure. In particular, the "competitive substance" refers to a substance that has the function of promoting the formation and cleavage of reversible bonds formed in the crosslinked structure. More specifically, a substance that is capable of reversibly bonding to a reversibly bondable functional group possessed by the polymer chain in the crosslinked structure can be referred to as a "competitive substance."

The competitive substance is particularly preferably a compound that is less likely to have effect on properties, lifetime, etc., of cells.

The competitive substance may be the same as or different from the molecule capable of forming a reversibly bondable group possessed by the crosslinked structure.

When a competitive substance is added to the polymer gel, reversible bonds, which form crosslinking points of polymer chains, are cleaved, and groups that previously formed the reversible bonds can reversibly bond to the competitive substance added. This changes the number of crosslinking points of the crosslinked structure, which results in changes in stiffness of the polymer gel, such as elastic modulus of the polymer gel.

When the polymer gel comprises a crosslinked structure in which the reversible bonds are bonds between host groups and guest groups (host-guest interactions), the competitive substance can be, for example, at least either host molecules or guest molecules. The host molecules or the guest molecules as the competitive substance may be the same as the host molecules or the guest molecules bonding to the polymer chains, or may be molecules that have a structure different therefrom.

Figure 1:
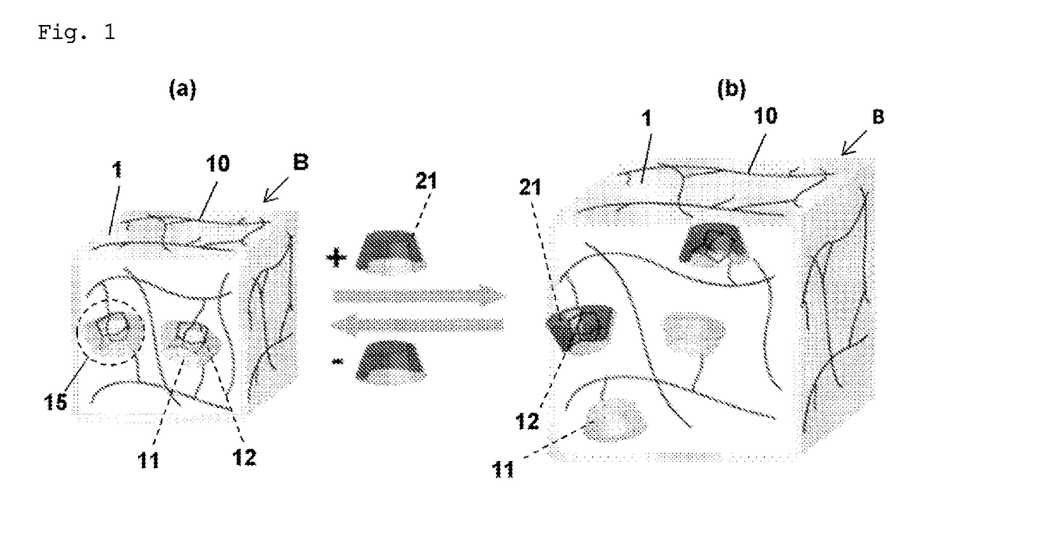
FIG. 1 is a schematic diagram illustrating host-guest interactions formed in the crosslinked structure.

FIG. 1 is a diagram schematically illustrating changes in the number of crosslinking points formed by host-guest interactions in the crosslinked structure due to the presence of a competitive substance. More specifically, FIG. 1 shows polymer gel B in a state (FIG. 1(a)); changes in crosslinking points at the time of adding a competitive substance thereto (FIG. 1(b)); and changes in crosslinking points at the time of removing the competitive substance therefrom.

As shown in FIG. 1(a), polymer gel B in the above state comprises a crosslinked structure 1. The crosslinked structure 1 is a crosslinked product in which polymer chains 10 having host groups 11 and guest groups 12 in side chains are crosslinked. This crosslinked product has a crosslinking point 15 formed by a host-guest interaction between a host group 11 and a guest group 12 (the dashed circle in FIG. 1(a)). The host group 11 is, for example, a group produced by removing one hydrogen atom from β-cyclodextrin, and the guest group 12 is, for example, a group produced by removing one hydrogen atom from adamantane.

When a host molecule 21 as a competitive substance is added to such polymer gel B, the host molecule 21 bonds to a guest molecule 12 (guest group) bonding to a polymer chain; that is, a host-guest interaction occurs, as shown in FIG. 1(b). As a result, the crosslinking point 15 formed by a host-guest interaction between the host molecule 11 (host group) and the guest molecule 12 (guest group) is lost. In FIG. 1, the host molecule 21 is β-cyclodextrin.

In this way, the number of crosslinking points in the crosslinked structure is reduced, which causes changes in elastic modulus of the polymer gel itself.

In FIG. 1(b), even when a guest molecule is added in place of the host molecule 21 as a competitive substance, the crosslinking point 15 is similarly lost, and the guest molecule as a competitive substance forms a host-guest interaction with the host group 11 bonding to a polymer chain.

The method for incorporating a competitive substance into the polymer gel is not particularly limited. A competitive substance can be incorporated into the polymer gel, for example, by immersing the polymer gel in a liquid containing a competitive substance. This method is hereinafter sometimes referred to as the "immersion method." The liquid containing a competitive substance is referred to as "liquid A." According to this immersion method, a competitive substance permeates the crosslinked structure in the polymer gel. Accordingly, the mass of the competitive substance contained in the polymer gel can be controlled by adjusting the concentration of the competitive substance in liquid A. This can change the number of crosslinking points in the crosslinked structure, thus controlling the stiffness of the polymer gel.

The kind of liquid A used in the immersion method is not particularly limited. Liquid A can be, for example, the same as the solvent contained in the polymer gel. Of course, liquid A used in the immersion method can be of a kind different from the solvent contained in the polymer gel. Liquid A used in the immersion method can contain two or more kinds of solvents. Alternatively, liquid A used in the immersion method may contain a culture fluid containing cells to be cultured in a medium.

According to the above immersion method, the polymer gel is immersed in a solvent or a culture fluid, and a competitive substance is added, either directly or in a state dissolved in a solvent, to the solvent or the culture fluid in which the polymer gel is in a immersed state, thereby allowing the polymer gel to contain the competitive substance. Alternatively, liquid A is prepared beforehand, and the polymer gel is immersed in liquid A to thereby allow the polymer gel to contain a competitive substance. The method for preparing liquid A is not particularly limited. For example, a method of directly adding a competitive substance can be used.

Liquid A can be continuously added via a liquid feed pump to a solvent in which the polymer gel is in an immersed state. By adjusting the concentration of the competitive substance to be fed, the concentration of the competitive substance in liquid A in which the polymer gel is in an immersed state can be continuously changed, and the concentration of the competitive substance contained in the polymer gel can be controlled by a simple method.

When the concentration of the competitive substance is reduced, for example, by removing the competitive substance from the polymer gel containing the competitive substance, reversible bonds are formed again, and crosslinks are formed. This can recover the stiffness of the polymer gel and thus restore the stiffness (elastic modulus) of the polymer gel to the original state, or make the stiffness closer to the original state. In this way, since the stiffness of the polymer gel can be reversibly changed by adjusting the concentration of the competitive substance in the polymer gel, the stiffness (elastic modulus) of the polymer gel according to this embodiment can be dynamically controlled. In the present specification, "dynamically controlling" the stiffness of the polymer gel means that the mechanical property of the polymer gel can be changed and adjusted over time; and "statically controlling" the stiffness of the polymer gel means that the mechanical property of the polymer gel cannot be changed or adjusted from the initial state.

The method of reducing the concentration of the competitive substance in the polymer gel can be, for example, by washing the polymer gel with a solvent containing no competitive substance, or replacing the solvent contained in the polymer gel with a solvent not containing a competitive substance. Alternatively, when the above liquid feed pump is used, the concentration of the competitive substance can be reduced by feeding, via the liquid feed pump, a competitive substance-free solvent in place of liquid A containing a competitive substance, so as to dilute liquid A in which the polymer gel is in an immersed state.

Medium

The medium according to this embodiment contains the polymer gel. The polymer gel for a medium is a material that can function as a support for culturing cells in a medium. The form of the medium is not limited, as long as it contains the polymer gel as a substrate. For example, the substrate for culturing cells can consist only of the polymer gel according to this embodiment, or can comprise a combination of the polymer gel and one or more other members. Alternatively, the medium can be formed by immersing the polymer gel in a culture fluid. Alternatively, the medium can be formed by subjecting the polymer gel to, for example, dehydration under reduced pressure or freeze-drying to reduce or remove the solvent and thereby form a dry gel (e.g., xerogel), and then adding a culture fluid so as to swell the gel again.

The composition of the culture fluid is not particularly limited, and can be the same as, for example, the composition of a known culture fluid. The culture fluid can further contain known components, such as sugar, lipids, amino acids, minerals, vitamins, and like nutrients for cell culture; components that function as growth factors for cell culture; migratory factors that allow cells to migrate; pH adjusters; and the like.

Since the above medium contains the polymer gel and can easily control stiffness of the polymer gel as a substrate by the above method, the stiffness of the medium can be controlled. Merely for annotation, the "stiffness of the medium" in this specification specifically refers to the elastic modulus of a substrate that supports cell culture. Since the stiffness of the substrate can, in particular, significantly affect cell differentiation and cell cycle in cell culture, the above substrate, which can freely control the stiffness, enables the control of cell differentiation, cell cycle, cell growth, cell morphology, etc.

The kind of cells that can be cultured in the medium according to this embodiment is not particularly limited. Examples include undifferentiated cells such as stem cells; differentiating cells such as myoblasts; more differentiated cells such as fibroblasts; and terminally differentiated cells. The cells can be primary cultured cells, or cells of cell lines. Culturing undifferentiated cells by using the polymer gel substrate according to this embodiment can dynamically control the cell cycle, more specifically, differentiation, cell growth without differentiation, etc. Examples of undifferentiated cells include zygote; pluripotent stem cells, such as embryonic stem cells (ES cells) and artificial pluripotent stem cells (iPS cells); trophectoderm stem cells (TS cells), extraembryonic endoderm cells (XEN cells), epiblast stem cells, and mesenchymal stem cells; hematopoietic stem cells; adipose-derived stem cells; sperm stem cells (GS cells); dental pulp stem cells; neural stem cells; pancreatic stem cells; hepatic stem cells; skin stem cells; cancer stem cells; and the like. Examples of cells that are more differentiated than stem cells include progenitor cells. Examples of progenitor cells include pancreatic progenitor cells and neural progenitor cells. Examples of terminally differentiated cells include nerve cells, muscle cells, and hepatocytes. The cells can be used alone, or in a combination of two or more.

Further, a kit for cell culture can also be produced by using the substrate according to this embodiment. Such a kit, which contains the substrate described above, is suitable for cell culture.

Method of Culturing Cells

The method of culturing the cells is not particularly limited, and can be performed by a known method. In particular, since the substrate has a feature of being capable of controlling the stiffness, cells can be cultured while changing the stiffness of the substrate, for example, in the following manner.

First, the substrate comprising the polymer gel is prepared. For example, the polymer gel is accommodated in a container, such as a petri dish, and conditioned in a cell culture fluid (cell culture medium) or the like to thereby obtain a polymer gel immersed in a liquid (e.g., liquid A described above).

When the gel is immersed in a liquid, such as a culture fluid, the solvent contained in the polymer gel can be replaced. This solvent replacement can be performed by a known method. The solvent that is contained in the polymer gel after the replacement can be, for example, the same as the solvent of the culture fluid.

The substrate is fabricated in the manner described above, and cells are cultured.

Subsequently, to change the stiffness of the polymer gel, a competitive substance is added to a fluid in which the polymer gel is in an immersed state. The competitive substance can be added to the fluid directly, or after the competitive substance is dissolved or diluted. It is also possible to continuously add the competitive substance via a liquid feed pump to a fluid in which the polymer gel is in an immersed state. More specifically, a container in which the polymer gel is accommodated is provided with an inlet and an outlet, and a liquid feed pump is connected to the inlet so as to continuously add a liquid containing a competitive substance to the fluid. The liquid fed into the container can be discharged from the outlet, as needed.

When a competitive substance is added to the fluid in this manner, the number of crosslinking points of the crosslinked structure in the polymer gel decreases, which can change the stiffness of the substrate.

The method for culturing cells according to this embodiment, which comprises an operation of adding to a cell culture liquid a competitive substance that inhibits the formation of reversible bonds, can change the stiffness of the substrate in which cells are cultured. Therefore, the method can adjust the stiffness of the substrate on the spot, which enables the observation of the dynamic response of cells.

Further, when the concentration of the competitive substance added to the cell culture fluid is reduced, crosslinks are again formed by reversible bonds between polymer chains of the crosslinked structure in the polymer gel. Therefore, the stiffness of the polymer gel can be gradually recovered. This enables reversible control of cell culture behaviors.

The method for decreasing the concentration of the competitive substance may be, for example, a method comprising adding a competitive substance-free liquid (e.g., a culture fluid not containing a competitive substance) to a cell culture fluid by using, for example, a liquid feed pump as described above to replace the liquid in the substrate therewith. This dilutes the competitive substance contained in the cell culture medium, thus reducing the concentration of the competitive substance.

After the concentration of the competitive substance is decreased, an operation of increasing the concentration of the competitive substance can be further performed in the same manner as described above. In this way, the operation of increasing the concentration of the competitive substance and the operation of decreasing the concentration of the competitive substance can be performed repeatedly.

As disclosed above, the cell culture method according to this embodiment can freely change the stiffness of the cell culture substrate by performing the operation of decreasing the concentration of a competitive substance in the medium, and the operation of increasing the concentration of the competitive substance in the medium. This can dynamically change cell culture behaviors.

The concentration of the competitive substance contained in the medium is preferably adjusted to a range of 10 mol/L or less. As long as the amount of competitive substance can be adjusted to this range, the stiffness of the gel can be within the range suitable for stable cell culture. The concentration of the competitive substance referred to herein means a concentration of the competitive substance relative to the liquid in which the polymer gel is immersed.

The concentration of the competitive substance can be adjusted to a range of 1 mol/L or less, and more preferably 0.05 mol/L or less. The lower limit of the concentration of the competitive substance may be, for example, but is not limited to, 0.0001 mol/L.

As disclosed above, because the method for culturing cells according to this embodiment can reversibly control cell culture behaviors, the method can be expected to establish a non-conventional technique for controlling cell differentiation. Furthermore, because this method enables the modulation of the substrate stiffness by adjusting the concentration of the competitive substance, the method can control cell culture behaviors under conditions that do not affect cells.

EXAMPLES

The following describes the present invention in more detail with reference to Examples. However, the present invention is not limited to the embodiments described in these Examples.

Preparation Example 1: Preparation of Polymer Gel Substrate

Figure 2:
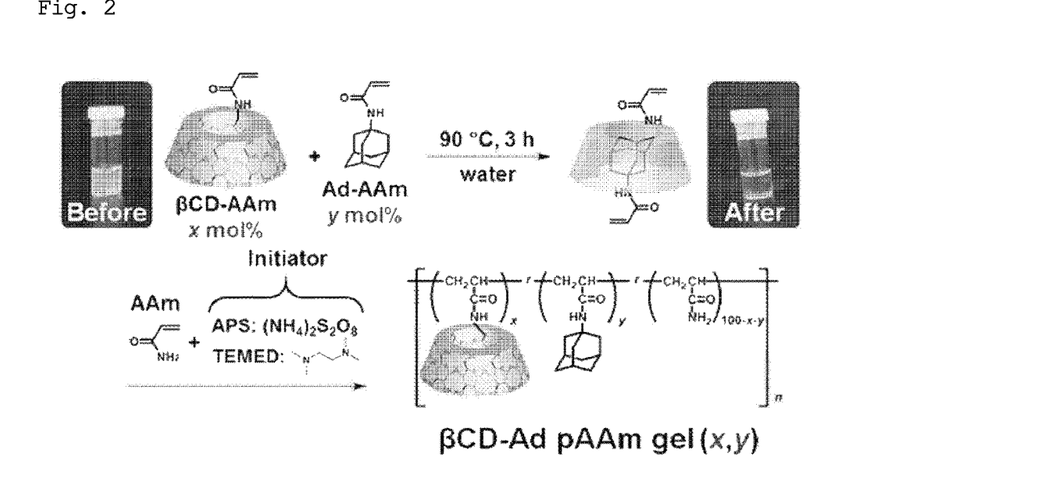
FIG. 2 is a reaction scheme showing an example of the method for producing the polymer gel.

A polymer gel was produced in accordance with the reaction scheme shown in FIG. 2.

Specifically, 6-acrylamide-β-cyclodextrin ((βCD-AAm) as a host group-containing polymerizable monomer (monomer (1)) and N-(1-adamantyl)acrylamide (Ad-AAm) as a guest group-containing polymerizable monomer (monomer (2)) were mixed in water to a concentration of each component of 40 mmol/kg. This mixture was stirred in a sealed container at 90° C. for 3 hours. The obtained mixture was allowed to cool to room temperature. Acrylamide as a monomer (3) was dissolved therein to a concentration of 1.92 mol/kg, thus preparing a solution having a total polymerizable monomer concentration of 2 mol/kg.

Ammonium persulfate as a polymerization initiator was then added to a concentration of 20 mmol/kg, and N,N,N',N'-tetramethylethylenediamine was added to a concentration of 20 mmol/kg in this order. The resulting mixture was thinly spread on a glass substrate and allowed to stand for 1 hour for the progress of gelation, thus obtaining a crosslinked structure, which was crosslinked by reversible bonds between host groups and guest groups. The crosslinked structure thus obtained was washed with a mixed solvent of dimethyl sulfoxide (DMSO) and water while replacing the solvent contained in the crosslinked structure, and the solvent contained in the crosslinked structure was finally replaced with water to produce a polymer gel having a thickness of 70 μm and a square area of 25 mm×25 mm. The polymer gel contained 2 mol % of βCD-AAm-derived repeating units and 2 mol % of Ad-AAm-derived repeating units in the polymer. FIG. 2 indicates βCD-Ad gel (x, y) in which x represents mol % of the host group-containing polymerizable monomer and y represents mol % of the guest group-containing polymerizable monomer, based on the total amount of all the polymerizable monomers.

Test Example 1: Measurement of Elastic Modulus

The polymer gel prepared in Preparation Example 1 was immobilized on a plastic dish having an inlet on one side and an outlet on the opposite side, and having a diameter of 35 mm. A Roswell Park Memorial Institute medium (hereinafter referred to as "RPMI medium") was added thereto to immerse the polymer gel, and a test was started. The elastic modulus of the polymer gel was measured every 10 minutes after the start of the experiment. The elastic modulus was measured using an atomic force microscope (AFM). More specifically, a cantilever was pressed into the polymer gel, and the elastic modulus was calculated based on the displacement and strain of the cantilever at the time of pressing.

Figure 3:
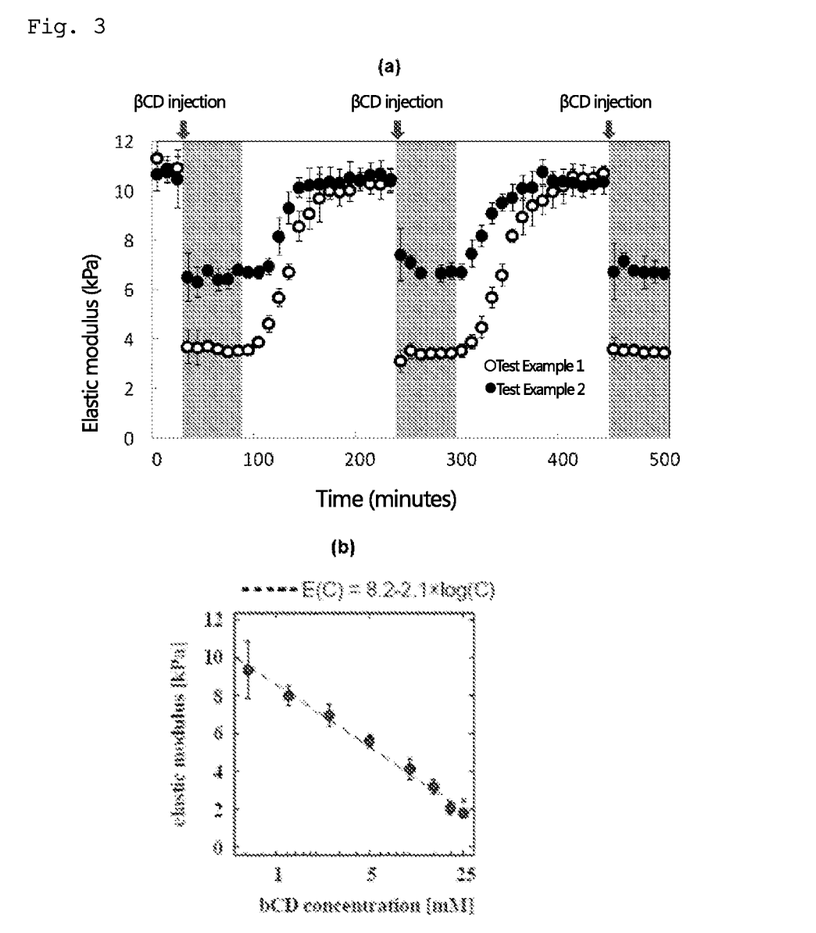
FIG. 3(a) is a graph showing the results of measuring changes in stiffness of the medium over time.
FIG. 3(b) is a graph showing the relationship between the concentration of the competitive substance and Young's modulus of the polymer gel.

Twenty-five minutes after the start of the test, an RPMI medium containing 10 mM β-CD was added from the inlet to replace the solution in the dish therewith, and maintained until 85 minutes after the start of the test. After 85 minutes had passed, an RPMI medium not containing β-CD was injected to replace the solution in the dish therewith, and maintained until 235 minutes after the start of the test. Similarly, an RPMI medium containing 10 mM β-CD was injected and maintained for a period of from 235 to 295 minutes after the start of the test; an RPMI medium not containing β-CD was injected and maintained for a period of from 295 to 445 minutes after the start of the test; and an RPMI medium containing 10 mM β-CD was injected again 445 minutes after the start of the test. In FIG. 3(a), the measurement results of the elastic modulus are represented by white circles. In this test, the RPMI medium containing β-CD and the RPMI medium not containing β-CD were both injected at a flow rate of 4.3 mL/min.

Test Example 2

The elastic modulus was measured in the same manner as in Test Example 1, except that an RPMI medium containing 2.5 mM β-CD was used in place of the RPMI medium containing 10 mM β-CD. The results are represented by black circles in FIG. 3(a).

The test results of Test Examples 1 and 2 show that the presence of a competitive substance β-CD in the solution decreases the number of crosslinking points in the crosslinked structure, and reduces the elastic modulus of the polymer gel; that the higher the β-CD concentration, the greater the reduction of elastic modulus; and that the elastic modulus of the polymer gel changes according to an increase or decrease of the β-CD concentration in the solution, that is, the elastic modulus of the polymer gel can be dynamically controlled.

Test Example 3

The polymer gel prepared in Preparation Example 1 was immobilized on the same plastic dish as used in Test Example 1, and allowed to stand in an RPMI medium not containing β-CD. An RPMI medium containing 0.5 mM β-CD was then added from the inlet to replace the solution in the dish therewith. The elastic modulus of the polymer gel was measured in the same manner as in Test Example 1. Using RPMI media each containing β-CD in a concentration of 1 mM, 2 mM, 5 mM, 10 mM, 15 mM, 20 mM, or 25 mM, the elastic modulus was measured in the same manner. FIG. 3(b) shows the results of plotting the elastic modulus on the ordinate and the β-CD concentration on the abscissa on the logarithmic scale. The results shown in FIG. 3(b) clearly indicate that when the concentration of the competitive substance β-CD increases, the number of crosslinking points in the crosslinked structure decreases, whereby the elastic modulus of the polymer gel decreases logarithmically. That is, the results show that the elastic modulus of the polymer gel can be dynamically controlled to a desired value by adjusting, for example, the amount and concentration of β-CD added.

Test Example 4: Morphological Observation of Mouse Myoblasts

The polymer gel obtained in Preparation Example 1 was immobilized on the same plastic dish as used in Test Example 1. Subsequently, an RPMI-1640 medium containing 10% fetal bovine serum penicillin and streptomycin (hereinafter referred to as "RPMI medium not containing β-CD") was injected into the dish, and 10000 mouse myoblasts (C2C12) were seeded therein and incubated for 24 hours until the start of measurement.

Figure 4:
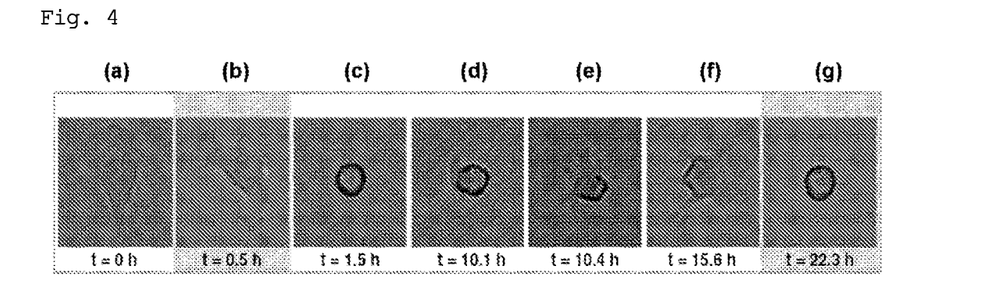
FIG. 4 is a presentation of the results of microscopically observing morphological changes of cultured cells over time.

The cell morphology was observed and imaged using an inverted microscope (IX81, produced by Olympus Corporation). FIG. 4 shows, from the left side, photographs of cells taken at the start of the measurement (FIG. 4(a)), at 0.5 hours after the start of the measurement (FIG. 4(b)), at 1.5 hours after the start of the measurement (FIG. 4(c)), at 10.1 hours after the start of the measurement (FIG. 4(d)), at 10.4 hours after the start of the measurement (FIG. 4(e)), at 15.6 hours after the start of the measurement (FIG. 4(f)), and at 22.3 hours after the start of the measurement (FIG. 4(g)). The length of one side of each photograph corresponds to 108 μm. In this measurement, from 30 minutes after the start of the measurement, an RPMI medium containing 10 mM β-CD was added from the inlet to replace the solution in the dish therewith, and maintained until 2 hours after the start of the measurement. Thereafter, an RPMI medium not containing β-CD was injected, and the polymer gel was maintained to have a high elastic modulus (i.e., be in a hard state) until 20 hours after the start of the measurement. Subsequently, an RPMI medium containing 10 mM β-CD was injected, and the polymer gel was maintained to have a low elastic modulus (i.e., be in a soft state) until 24 hours after the start of the measurement.

When the polymer gel had a high elastic modulus (i.e. was in a hard state) immediately after the start of the measurement or 30 minutes after the start of the measurement, the cells were in a spread state, as is clear from the two photographs of FIGS. 4(a) and (b). In contrast, when the elastic modulus of the polymer gel was reduced 1.5 hours after the start of the measurement (FIG. 4(c)), the cells were transformed into a round shape. Eight hours after the elastic modulus of the polymer gel was increased again (i.e., 10.1 hours after the start of the measurement), the cells remained round, as shown in FIG. 4(d). However, 10.4 hours after the start of the measurement (FIG. 4(e)), the cells suddenly started to transform into a spread. After about 15 hours passed, the cells widely spread, as is clear from FIG. 4(f). When the elastic modulus of the polymer gel was reduced again 22.3 hours after the start of the measurement, the cells became round again, as is clear from FIG. 4(g).

The above results reveal that when the polymer gel has a high elastic modulus (i.e. is hard), the cells are in a spread configuration; that when a competitive substance is added and the polymer gel has a low elastic modulus (i.e., is soft), the cells become closer to a spherical shape; that such morphological changes can be repeated; and that changing from a spherical shape to a spread configuration particularly takes time.

Test Example 5

Figure 5:
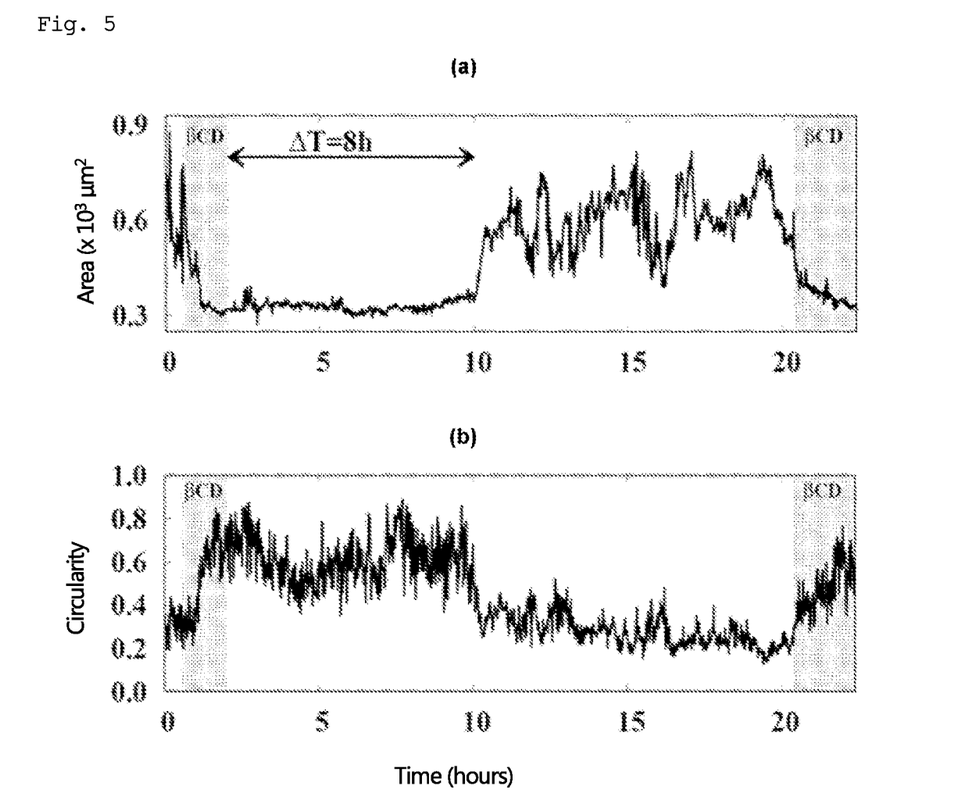
FIG. 5(a) is a graph showing changes in cell area.
FIG. 5(b) is a graph showing changes in circularity of cells.

Concurrent with the observation in Test Example 4, digital data were binarized to determine the cell area and cell circularity. FIG. 5(a) shows the cell area, and FIG. 5(b) shows the cell circularity. The cell circularity was calculated according to the following formula:

$$(4\Pi \times \text{Area})/\{(\text{Outer circumferential length of cells})^2\}.$$

As the circularity is closer to 1, the cells are closer to a circle in shape.

The results shown in FIG. 5(a) and FIG. 5(b) clearly indicate that when the elastic modulus of the polymer gel is reduced (the shaded regions indicated as βCD in FIG. 5(a) and FIG. 5(b)), the cells relatively quickly transform to a round shape and the cell area also decreases; and that when the elastic modulus of the polymer gel changed from low to high, the cells do not immediately transform and the cell area remains unchanged for a while, and after the passage of a certain period of time, the cells rapidly transform. Further, when the elastic modulus of the polymer gel was reduced again 20 hours after the start of the measurement, the cells became closer to a round shape again. The results thus show that cell morphology can be changed by changing the elasticity of the polymer gel of the present invention; that is, cell properties and shape can be dynamically controlled by culturing the cells using the polymer gel of the present invention.

Figure 6:
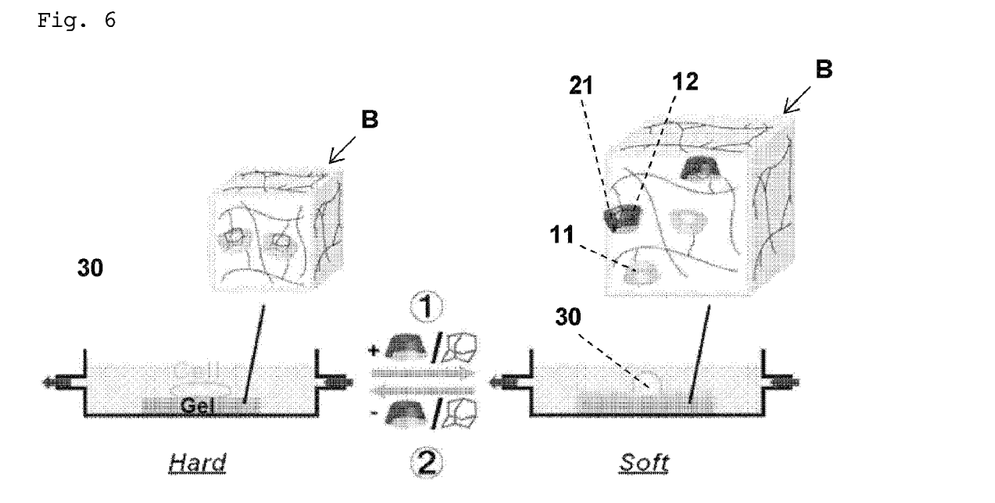
FIG. 6 is a schematic diagram illustrating the conditions in Test Examples 4 and 5.

FIG. 6 is a schematic diagram illustrating how Test Examples 4 and 5 described above proceed. As shown in FIG. 6, when the concentration of a competitive substance is low and the substrate is in a stiff state, the cells have a spread morphology. Conversely, when the substrate is in a soft state, the cells exhibit a contracted, closer-to-spherical morphology.

The above results show that the polymer gel enables the reversible control of cell morphology and function according to the stiffness of the gel substrate.

The invention claimed is:

1. A cell culture method comprising culturing cells in a medium, the medium comprising a cell culture substrate comprising a polymer gel, the polymer gel comprising a solvent and a crosslinked structure that is crosslinked by reversible bonds,
   the method further comprising adding to the medium a competitive substance having a property of inhibiting formation of the reversible bonds, and adjusting the concentration of the competitive substance added to the medium,
   wherein the competitive substance having a property of reversibly controlling crosslinking density by competitively bonding to a reversibly bondable functional group possessed by a polymer chain of the crosslinked structure in the polymer gel.

2. The cell culture method according to claim 1, wherein the concentration of the competitive substance contained in the medium is adjusted to between 0.0001 mol/L and 10 mol/L.

3. The cell culture method according to claim 1, wherein the reversible bonds are bonds between host groups and guest groups in the crosslinked structure, wherein the reversible bonds are at least one member selected from the group consisting of hydrophobic interactions, hydrogen bonds, ionic bonds, coordinate bonds, Π-electron interactions, and intermolecular interactions other than these.

4. The cell culture method according to claim 3, wherein the crosslinked structure is a polymer comprising:

a repeating structural unit represented by formula (1a)

(1a)

wherein Ra is hydrogen or methyl; $R^1$ is a divalent group formed by removing one hydrogen atom from a monovalent group selected from the group consisting of hydroxyl, thiol, alkoxy optionally having one or more substituents, thioalkoxy optionally having one or more substituents, alkyl optionally having one or more substituents, amino optionally having one substituent, amide optionally having one or more substituents, aldehyde, and carboxyl; and $R^4$ is a host group;

a repeating structural unit represented by formula (2a):

(2a)

wherein Ra is as defined above in formula (1a), that is, Ra is hydrogen or methyl; $R^2$ is a divalent group formed by removing one hydrogen atom from a monovalent group selected from the group consisting of hydroxyl, thiol, alkoxy optionally having one or more substituents, thioalkoxy optionally having one or more substituents, alkyl optionally having one or more substituents, amino optionally having one substituent, amide optionally having one or more substituents, aldehyde, and carboxyl; and $R^B$ is a guest group; and a repeating structural unit represented by formula (3a):

(3a)

wherein Ra is as defined above in formula (1a); $R^3$ is halogen, hydroxyl, thiol, amino optionally having one substituent, carboxyl optionally having one substituent, or amide optionally having one or more substituents.

* * * * *